(12) United States Patent
Walsh et al.

(10) Patent No.: US 9,242,100 B2
(45) Date of Patent: Jan. 26, 2016

(54) OPTICAL FIBER-FINE WIRE LEAD FOR ELECTROSTIMULATION AND SENSING

(71) Applicant: Cardia Access, Inc., Eden Prairie, MN (US)

(72) Inventors: Robert Gilmore Walsh, Newport, OR (US); Jin Shimada, Grantsburg, WI (US); Michael E. Grant, Cambridge, MN (US); James E. Shapland, Vadnais Heights, MN (US)

(73) Assignee: NuAx, Inc., Minnetonka, MN (US)

(\*) Notice: Subject to any disclaimer, the term of this patent is extended or adjusted under 35 U.S.C. 154(b) by 0 days.

(21) Appl. No.: 13/831,001

(22) Filed: Mar. 14, 2013

(65) Prior Publication Data

US 2014/0155948 A1 Jun. 5, 2014

Related U.S. Application Data

(60) Provisional application No. 61/742,280, filed on Aug. 7, 2012.

(51) Int. Cl.

| | |
|---|---|
| *A61N 1/36* | (2006.01) |
| *A61N 1/365* | (2006.01) |
| *A61N 1/372* | (2006.01) |
| *A61N 1/39* | (2006.01) |
| *A61B 5/00* | (2006.01) |
| *A61B 5/0215* | (2006.01) |

(52) U.S. Cl.
CPC .......... *A61N 1/36514* (2013.01); *A61B 5/0084* (2013.01); *A61B 5/02154* (2013.01); *A61B 5/6852* (2013.01); *A61N 1/3655* (2013.01); *A61N 1/36564* (2013.01); *A61N 1/36571* (2013.01); *A61N 1/37211* (2013.01); *A61N 1/3987* (2013.01)

(58) Field of Classification Search
CPC ............. A61B 5/0084; A61B 5/02154; A61B 5/6852; A61N 1/36514; A61N 1/3655; A61N 1/36564; A61N 1/36571; A61N 1/37211; A61N 1/3987; G02B 6/3817; G02B 6/4416
USPC .................................................. 607/116–118
See application file for complete search history.

(56) References Cited

U.S. PATENT DOCUMENTS

| | | |
|---|---|---|
| 3,980,806 A | 9/1976 | May |
| 4,276,144 A | 6/1981 | Hahn |
| 4,407,561 A | 10/1983 | Wysocki |
| 4,408,604 A | 10/1983 | Hirshorn et al. |
| 4,418,984 A | 12/1983 | Wysocki et al. |
| 4,575,187 A | 3/1986 | Howard et al. |
| 4,785,815 A | 11/1988 | Cohen |
| 4,791,575 A | 12/1988 | Gupta et al. |
| 4,798,206 A | 1/1989 | Maddison et al. |
| 4,873,989 A | 10/1989 | Einzig |

(Continued)

*Primary Examiner* — Amanda Patton
(74) *Attorney, Agent, or Firm* — John M. Berns

(57) ABSTRACT

Various aspects of the present disclosure are directed toward an implantable electrostimulation device, a plurality of sensing and pacing elements, and a fine wire lead extending in a sealed relationship from the electrostimulation device and to the plurality of sensing and pacing elements. The fine wire lead includes multiple discrete conductors and a drawn silica or glass fiber core, a polymer cladding on the drawn silica or glass fiber core, and a conductive metal cladding over the polymer cladding. Additionally, the fine wire lead simultaneously delivers different electrical signals or optical signals between the sensing and pacing elements and the electrostimulation device.

20 Claims, 18 Drawing Sheets

(56) References Cited

U.S. PATENT DOCUMENTS

| | | | |
|---|---|---|---|
| 4,896,209 A | 1/1990 | Matsuzaki | |
| 4,911,712 A | 3/1990 | Harrington | |
| 5,117,828 A | 6/1992 | Metzger et al. | |
| 5,218,171 A | 6/1993 | Aldissi | |
| 5,433,744 A | 7/1995 | Breyen et al. | |
| 5,463,138 A | 10/1995 | Muller | |
| 5,500,012 A | 3/1996 | Brucker et al. | |
| 5,531,779 A | 7/1996 | Dahl et al. | |
| 5,750,930 A | 5/1998 | Buck et al. | |
| 6,104,961 A | 8/2000 | Conger et al. | |
| 6,129,685 A | 10/2000 | Howard | |
| 6,167,314 A | 12/2000 | Fischer et al. | |
| 6,178,356 B1 | 1/2001 | Chastain et al. | |
| 6,195,411 B1 | 2/2001 | Dinsmore | |
| 6,319,188 B1 | 11/2001 | Lovoi | |
| 6,356,791 B1 | 3/2002 | Westlund et al. | |
| 6,366,819 B1 | 4/2002 | Stokes | |
| 6,456,888 B1 | 9/2002 | Skinner et al. | |
| 6,564,107 B1 | 5/2003 | Bodner et al. | |
| 6,697,676 B2 | 2/2004 | Dahl et al. | |
| 6,711,443 B2 | 3/2004 | Osypka | |
| 6,792,316 B2 | 9/2004 | Sass | |
| 6,849,074 B2 | 2/2005 | Chen et al. | |
| 6,879,861 B2 | 4/2005 | Benz et al. | |
| 6,930,242 B1 | 8/2005 | Helfer et al. | |
| 7,010,356 B2 | 3/2006 | Jog et al. | |
| 7,077,837 B2 | 7/2006 | Sahagian | |
| 7,079,902 B2 | 7/2006 | Soukup et al. | |
| 7,137,395 B2 | 11/2006 | Fried et al. | |
| 7,231,260 B2 | 6/2007 | Wallace et al. | |
| 7,420,124 B2 | 9/2008 | Michael et al. | |
| 7,519,432 B2 | 4/2009 | Bolea et al. | |
| 7,865,044 B2 | 1/2011 | Farhadiroushan et al. | |
| 7,883,536 B1 * | 2/2011 | Bendett et al. | 607/89 |
| 7,917,213 B2 | 3/2011 | Bulkes et al. | |
| 8,000,808 B2 | 8/2011 | Hegland et al. | |
| 2001/0055904 A1 | 12/2001 | Sawada et al. | |
| 2002/0052636 A1 | 5/2002 | Bardy et al. | |
| 2002/0183818 A1 | 12/2002 | Williams et al. | |
| 2002/0189845 A1 | 12/2002 | Gorrell | |
| 2003/0077935 A1 | 4/2003 | Stein et al. | |
| 2003/0195602 A1 | 10/2003 | Boling | |
| 2003/0195603 A1 | 10/2003 | Scheiner | |
| 2004/0024440 A1 | 2/2004 | Cole | |
| 2004/0064174 A1 | 4/2004 | Belden | |
| 2004/0122499 A1 | 6/2004 | Westlund | |
| 2004/0243210 A1 | 12/2004 | Morgan et al. | |
| 2005/0090885 A1 | 4/2005 | Harris et al. | |
| 2005/0096720 A1 | 5/2005 | Sharma et al. | |
| 2005/0103932 A1 | 5/2005 | Huynh | |
| 2006/0009830 A1 | 1/2006 | Atkinson et al. | |
| 2006/0095105 A1 | 5/2006 | Jog et al. | |
| 2006/0106443 A1 | 5/2006 | Michael et al. | |
| 2006/0293741 A1 | 12/2006 | Johnson et al. | |
| 2007/0067000 A1 | 3/2007 | Strother et al. | |
| 2007/0088208 A1 | 4/2007 | Yasuzawa et al. | |
| 2007/0088417 A1 | 4/2007 | Schouenborg | |
| 2007/0288077 A1 | 12/2007 | Bulkes et al. | |
| 2007/0293923 A1 | 12/2007 | Soltis et al. | |
| 2008/0015625 A1 | 1/2008 | Ventura et al. | |
| 2008/0039916 A1 | 2/2008 | Colliou et al. | |
| 2008/0077220 A1 | 3/2008 | Reddy | |
| 2008/0097567 A1 | 4/2008 | Haldeman | |
| 2008/0183257 A1 | 7/2008 | Imran et al. | |
| 2008/0217587 A1 | 9/2008 | Gaudiana et al. | |
| 2008/0255629 A1 | 10/2008 | Jenson et al. | |
| 2009/0204193 A1 | 8/2009 | Kokones et al. | |
| 2009/0299446 A1 | 12/2009 | Lovoi et al. | |
| 2010/0057179 A1 | 3/2010 | Storey | |
| 2010/0114271 A1 | 5/2010 | Sommer et al. | |
| 2010/0182023 A1 | 7/2010 | Pena et al. | |
| 2010/0183269 A1 | 7/2010 | Mahapatra et al. | |
| 2010/0278491 A1 | 11/2010 | Noddings | |
| 2011/0220408 A1 | 9/2011 | Walsh et al. | |
| 2011/0245714 A1 * | 10/2011 | Volckaerts | 600/559 |
| 2011/0301657 A1 * | 12/2011 | Walsh et al. | 607/5 |
| 2012/0277600 A1 | 11/2012 | Greenhut | |
| 2013/0041447 A1 | 2/2013 | Erb et al. | |

* cited by examiner

OPTICAL FIBER-FINE WIRE LEAD FOR ELECTROSTIMULATION AND SENSING

Various aspects of the present disclosure are directed toward an optical fiber, fine wire conductor for use in electrostimulation and sensing devices such as cardiac pacemakers, ICD and CRT devices, neurostimulation devices. The disclosure encompasses an improved fine wire conductor for such devices, a lead of very small diameter and capable of repeated cycles of bending without fatigue or failure. The disclosure also encompasses an improved durable, fine wire conductor(s) and optical fiber(s) which has multiple conductors that can independently and concurrently transmit electrical and optical energy and/or data signals within a lead for electrostimulation and sensing.

The term therapeutic electrostimulation device (or similar) as used herein is intended to refer to all such implantable stimulation and/or sensing devices that employ wire leads. A fine wire lead consists of several key components, including a lead body, a proximal connector, and one or more distal electrodes, which are affixed to the lead body. This disclosure is also directed towards a silica or glass fine wire electrostimulation and sensing lead, capable of performing electrostimulation via a metallic conductor(s), while independently and concurrently performing fiber optic-based sensing or pacing functions.

Cardiac pacing has become a well-tested and effective therapy for maintaining heart function for patients with various heart conditions. Generally, pacing is done from a control unit placed under but near the skin surface for access and communications with the external controller/programmer when needed. Leads are routed from the controller to electrodes in contact with the heart to provide power for pacing and data from the electrodes/sensors to the controller.

Neurostimulation or neuromodulation refers to a therapy in which low voltage electrical stimulation is delivered to the spinal cord, targeted peripheral nerves or the brain in order to block, potentiate, or otherwise modulate neuroactivity. Neurostimulation has applications for numerous debilitating conditions, including treatment-resistant depression, epilepsy, gastroparesis, hearing loss, incontinence, chronic, untreatable pain, Parkinson's disease, essential tremor and dystonia. Other applications where neurostimulation holds promise include Alzheimer's disease, blindness, chronic migraines, morbid obesity, obsessive-compulsive disorder, paralysis, sleep apnea, stroke, and severe tinnitus.

Over 650,000 pacemakers are implanted in patients annually worldwide, including over 280,000 in the United States. Another approximately 100,000 have an ICD or CRT device. The pacemakers involve an average of about 1.4 implanted conductive leads, and the ICD and CRT devices use on average about 2.5 leads. These leads are necessarily implanted through tortuous pathways in the hostile environment of the human body. They are subjected to repeated flexing due to beating of the heart and the muscular movements associated with that beating, and also due to other movements in the upper body of the patient, movements that involve the pathway from the pacemaker to the heart. Previously available wire leads have not withstood these repeated flexings over long periods of time, and many have experienced failure due to the fatigue of repeated bending.

Today's pacing leads are typically referred to as multifilar, consisting of two or more wire coils that are wound in parallel together around a central axis in a spiral manner. The filar winding changes the overall stress vector in the conductor body from a bending stress in a straight wire to a torsion stress in a curved cylindrical wire perpendicular to lead axis. A straight wire can be put in overall tension, leading to fatigue failure, whereas a filar wound cannot. However, the bulk of the wire and the need to coil or twist the wires to reduce stress, limit the ability to produce smaller diameter leads Leads with electrodes are generally routed into the heart through the right, low pressure, side of the heart. However, resynchronization pacing involves pacing from the right side of the heart and from the high-pressure left ventricle. Since leads/electrodes cannot be positioned within the left ventricle, access for pacing the left side of the heart has involved routing lead wires from the right side of the heart through the coronary sinus and into veins draining the left side of the heart. This access path has the major drawback that the placement of the electrodes is limited since probes cannot reach into many desired locations due to the small diameter of these veins. Therefore, there is a need to have a durable, fatigue resistant, small diameter electrostimulation lead.

Modern day pacemakers and other electrostimulation devices are capable of responding to changes in physical exertion level or other physical parameters of patients. To accomplish this, artificial sensors are implanted which enable a feedback loop for adjusting pacemaker stimulation algorithms. As a result of these sensors, improved exertional tolerance can be achieved. Generally, sensors transmit signals through an electrical conductor, which may be synonymous with pacemaker leads that enable cardiac electrostimulation. However, a limited number of conductors can be included in current leads due to diameter limitations.

Pacing leads serve the dual functions of sensing of intrinsic cardiac signals as well as electrostimulation. The higher energy transmission of the pacing pulse often overwhelms the sensing function and/or causes cross talk between the lead's conductors. The pacemaker circuit can be designed to ignore the pacing pulse by turning off the sensing circuitry immediately after the pacing pulse, rendering the pacemaker blind during this time. Any intrinsic cardiac activity would not be sensed during this time period. This could cause significant errors for the pacemaker algorithm. Therefore, there is a need for a small diameter, robust and durable pacing lead with the capability of incorporating sensors through multiple and independent conductors.

It is the object of the present disclosure described herein to detail an improved multifunctional small diameter, fine wire glass or silica fiber lead with multiple conductors capable of multiple independent and concurrent electrostimulation and sensing.

SUMMARY

A flexible and durable fine wire lead for implanting in the body, with connection to a pacemaker, ICD, CRT or other electrostimulation pulse generator, is formed from a drawn silica, glass, or sapphire crystalline quartz fiber core with a conductive metal buffer cladding on the core. Additional structural details include the fact that a polymer coating can be layered under and/or over the metal buffer cladding, which may be used to introduce a hermetic seal to the fiber core to prevent environmental stress cracking or other mechanism of degradation associated with exposure and flexure within a biological system.

The outer diameter of the fine wire lead preferably is less than about 750 microns, and may be 200 microns or even as small as 50 microns. Metals employed in the buffer can include aluminum, gold, platinum, titanium, tantalum, silver, or others, as well as metal alloys of which MP35N, a nickel-cobalt based alloy is one example. In one example of metal cladding, a molten metal film, such as gold or silver is applied to the drawn silica, glass, or sapphire crystalline quartz fiber core immediately upon drawing and providing a protective hermetic seal over the silica, glass, or sapphire crystalline quartz fiber, forming a coaxial fine wire optical fiber. Alternatively, a thin layer of carbon may be coated on to the fiber core immediately after drawing the core. Alternatively, a thin film of polymer may be coated onto the fiber core, with or without a hermetic carbon underlayment. In these cases, a metallized conductor is deposited upon the carbon and/or polymer surface in a secondary process step.

Inherent in the concept of a metallized fine wire lead is the ability to use more than one metal in the construction of such leads. For instance, an initial metal layer may be deposited directly to the carbon layer overlying the glass or silica. Such deposition takes advantage of strong adhesion and fatigue resistance afforded by the carbon/metal bonding to produce a hermetic seal. Likewise, metal may be applied directly to a polymer underlayment. One or more additional metals or metal alloys could then be deposited on the first metal. The purpose the second metal would be to serve as the primary conductive material for carrying electrical current.

Alternatively, the silica or other type of fiber can be formed with a hollow center and can serve as a dielectric with a wire in the center of the fiber core as one conductor, and the metallic buffer layer on the outside of the fiber core providing fiber protection and acting as the coaxial second conductor or ground return. The flexibility of a composite structure consisting of multiple single conductor fibers can be enhanced by employing hollow fibers. A thin wall hollow fiber core will have greater flexural response for a given applied force, than a solid fiber core of the same material, and the same overall diameter.

The current disclosure includes embodiments to provide multiple discrete conductors that can be incorporated into a small diameter lead. Each discrete conductor would be electrically isolated from other conductors. Such discrete conductive pathways would allow the delivery of different electrical signals or energy at approximately the same time, thus defined as simultaneous delivery or transmission. The production of multiple discrete conductors can be accomplished by modifying the metal cladding along the length of the lead. Masking may be pre-applied to the carbon and/or polymer surface to enable a patterned coating of metal on the carbon and/or polymer surface. Such a pattern may be useful for creating two or more separate electrically conductive paths along the length of the fine wire lead, thus enabling fabrication of single, dual or multiple electrical conductors upon a single fine wire lead. The metal can be selectively removed by laser or another technique to produce multiple conductive paths along the length of the lead. Each independent electrical conductor can be attached to separate electrodes and/or sensors using independent radial attachment strips. The pattern of the conductive pathways can be applied in a specific pattern to accomplish other desired effects, such as applying it in a spiral pattern to provide shielding in order to reduce potential for electromagnetic interference. Such designs could be used for non-medical applications (i.e., aerospace applications) to provide light weight, durable, flexible multiple conductors for transmission of electrical and optical signals.

Whether fabricated from a solid or hollow core glass or silica fiber, such a fiber core structure can serve as the basis for fiber optic-based sensing and/or energy transmission. Optically based sensors could include those to measure strain, pressure, temperature, oxygen saturation, and other properties that modulate the intensity, phase, wavelength, polarization, or transit time of the light in the fiber. Optical sensors can also provide a spectroscopic feedback. Extrinsic optical sensors which use the optical fiber to transmit light to and from a non-fiber optical sensor or electrical sensor connected to an optical transmitter could be incorporated into various embodiments.

Various sensor elements (optical and/or electrical) can be mounted at desired locations along the fine wire lead of this disclosure, including at or near the distal terminal. Electrically based sensors include those to measure pressure, strain, temperature, fluid velocity/flow (Doppler) and other physical quantities. As a simple electrode, they can measure and monitor the intrinsic electrical activity of the heart or other anatomical regions. Although the sensors can be connected by way of an optical fiber, they are more commonly connected by way of an electrical conductor. Multiple sensors could be located along a catheter/guidewire to provide additional physiological input for diagnostic or therapeutic applications.

The optical based-sensors would be constructed such that they operate independently and concurrently with the electrostimulation and/or electrical-based sensing function of the lead. As such, electrostimulation would not interfere with optical based-sensing functions, and visa versa. As previously mentioned, hollow fibers may have several advantages over solid core fibers for use with the fine wire lead of this application. In addition, optical based communications may be less handicapped by attenuation with hollow fibers as compared to solid core fibers.

One example of a sensing function that might be desirable is that of a blood pressure sensor. In this example, a piezoelectric element would be mounted at a desired location upon the lead, with direct exposure to flowing blood. The piezoelectric element would be sensitive to constant change in blood pressure. The electrical signal generated by the piezoelectric element during the cycle of stress response to changes in blood pressure would be converted to light by employing a light emitting diode (LED) or similar device. The light energy would then be transmitted via the lead to a collector, which may be incorporated into the electrostimulation device, or in a separately implanted device, which would then convert the light signal to an electrical signal correlating with blood pressure. This signal could be used as input into a pacing algorithm, stored as diagnostic data, or passed by wireless transmission to a receiver outside the body, enabling a real-time read out of blood pressure, independent and concurrent with electrostimulation.

Other embodiments could include sensors in which pressure or another physiological parameter directly modulates the intensity, phase, wavelength, polarization, or transit time of the light in the fiber.

The optical fiber could also transmit optical signals for therapeutic uses, such as cardiac stimulation (pacing) or other electrostimulation. In one embodiment, a light generator would transmit an optical pulse through the optical fiber of the lead. A convertor at the distal end of the lead would receive the optical signal and convert the light energy into an electrical energy (similar to a silicon based photo cell). The converted electrical energy could be stored in a small capacitor and discharged as an electrical pulse. The electrical pulse would be conducted to an electrode located at the end of the lead and in contact with the heart. The electrical pulse would pace the heart (stimulate the heart to contract). The circuitry required to convert the light energy into a pacing pulse could be miniaturized to reside in the distal portion of the lead. The timing, amplitude, duration, and other specifics of the electrical pulse could be controlled by the generator with the control signals to the circuitry at the tip of the lead transmitted through other conductors within the lead.

The completed metallized lead body may be conveniently coated with a thin lubricious and protective polymeric material, such as Teflon, to provide necessary electrical insulation. Polyurethane or silicone may conveniently be used for such a jacketing material, providing biocompatibility and protection from the internal biochemical environment of the body.

The distal end of the glass/silica fine wire lead of this disclosure is compatible with a variety of anchoring systems for stabilizing the fiber lead against unwanted migration within the vasculature or heart. Such anchoring systems can consist of expandable/retractable stents attached to the lead, or helical, wavy, angled, corkscrew, J-hook or expandable loop-type extensions attached to the lead, that take on the desired anchoring shape after delivery of the lead from within a delivery catheter. The anchoring design could be used for positioning within the chamber of the heart or within a blood vein or other vessel within the body. The anchoring system could also incorporate various tip embodiments such as known in the cardiac pacing field.

It is among the objects of this disclosure to incorporate a fiber optic-based transmission, communication and/or sensing function onto a glass or silica fine wire electrostimulation lead, with the capability of operating concurrently with electrostimulation. Such a fiber optic-based transmission, communication and/or sensing function, independent of metal conductor-based electrostimulation and/or sensing, provides a new versatility to fine wire leads for operation with pacemakers, ICDs, CRTs, other cardiac pulse generators. Such disclosure can also be used as therapeutic and/or diagnostic electrostimulation or sensing leads in non-cardiac parts of the body, and can also be used in therapeutic and diagnostics guidewires, ablation catheters, and other medical devices requiring multiple sensor-based conductive pathways. In part, this is accomplished by the disclosure described herein, involving apparatus and methods for achieving an electrostimulation/sensing lead of small diameter but with multiple discrete and independent conductors for transmission of optical and/or electrical signals and pulses.

The above discussion/summary is not intended to describe each embodiment or every implementation of the present disclosure. The figures and detailed description that follow also exemplify various embodiments.

BRIEF DESCRIPTION OF THE DRAWINGS

Various example embodiments may be more completely understood in consideration of the following detailed description in connection with the accompanying drawings, in which.

Figure 1:
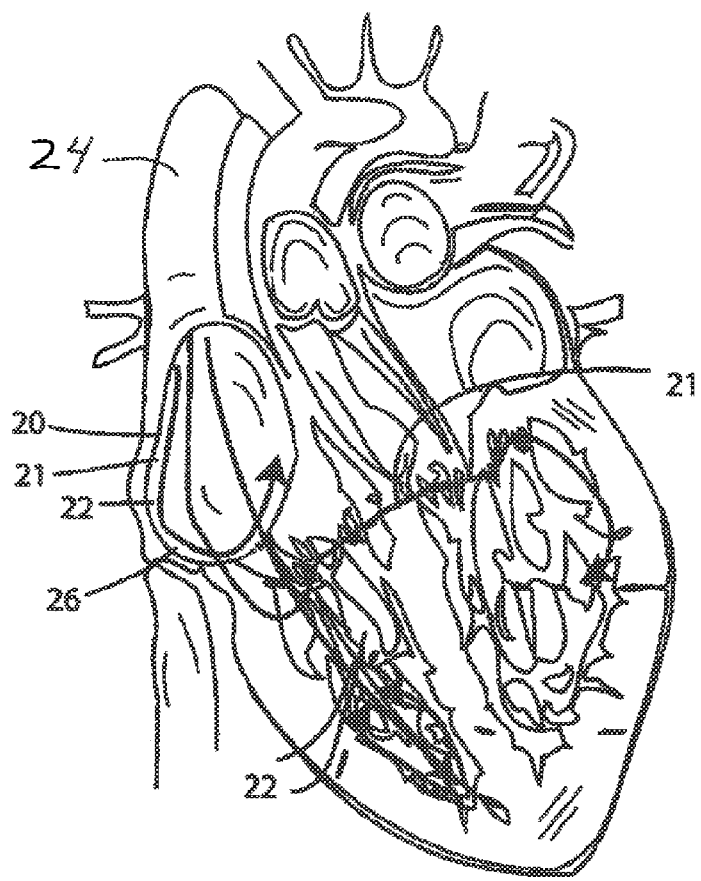
FIG. 1 is a schematic view partially cut away, showing a human heart, and indicating a path of a pacemaker or other cardiac pulse leads, in accordance with conventional practice.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the scope of the disclosure including aspects defined in the claims. In addition, the term "example" as used throughout this application is only by way of illustration, and not limitation.

DETAILED DESCRIPTION

Various aspects of the present disclosure are directed toward attachment of proximal connectors and distal electrodes on all implanted fine wire leads, but illustrated in the context of a cardiac pacing device. Typically, a pacemaker is implanted just under the skin and on the left side of the chest, near the shoulder. The pacemaker leads follow a somewhat tortuous path from the pacemaker through the venous system to the heart.

Various aspects of the present disclosure are directed toward apparatus and methods that include an implantable electrostimulation device, a plurality of sensing and pacing elements, and a fine wire lead extending in a sealed relationship from the electrostimulation device and to the plurality of sensing and pacing elements. The fine wire lead includes multiple discrete conductors and a drawn silica or glass fiber core, a polymer cladding on the drawn silica or glass fiber core, and a conductive metal cladding over the polymer cladding. Additionally, the fine wire lead simultaneously delivers different electrical signals or optical signals between the sensing and pacing elements and the electrostimulation device. In certain embodiments, the outer diameter of the fine wire lead at the metal layer is no greater than about 750 microns. Additionally, certain embodiments include a drawn silica or glass fiber core that has a diameter no greater than about 450 microns. Further, in other embodiments, the fine wire lead is sufficiently flexible to bend to a radius of about 8 to 10 times the drawn silica or glass fiber core diameter without damage.

Various aspects of the present disclosure are also directed toward apparatus and methods having an electrostimulation device, a plurality of sensing and pacing elements, and a fine wire lead. The fine wire lead includes a drawn glass or silica fiber core, a cladding (on the drawn glass or silica fiber core) having a carbon hermetic seal material thereon, and a conductive metal layer (on the cladding), arranged into multiple discrete conductors. Further, a biocompatible coating is provided to seal the fine wire lead. Additionally, the fine wire lead extends in a sealed relationship from the electrostimulation device and to the plurality of sensing and pacing elements. The fine wire lead simultaneously delivers different electrical signals or optical signals between the sensing and pacing elements and the electrostimulation device.

In certain embodiments of the present disclosure, the fine wire lead is proofed to at least about 90% of intrinsic strength value of the drawn silica or glass fiber core, and in other embodiments, the drawn silica or glass fiber core transmits optical signals between the electrostimulation device and at least one of the plurality of sensor elements and pacing element. Moreover, embodiments of the present disclosure are further characterized in that the metal cladding is a conductive metal that delivers electrical signals between the electrostimulation device and at least one of the plurality of sensor elements and pacing elements. Further, the fine wire lead can be covered by a biocompatible insulating coating. Various embodiments of the present disclosure also can have the conductive metal composed of silver, or, in other embodiments, the polymer cladding can be composed of carbon.

In various embodiments of the present disclosure, the implantable electrostimulation device is one of a cardiac pacemaker, cardioverter-defibrillator, cardiac resynchronization therapy device, and a control hub configured and arranged to interconnect to the fine wire conductor. Further, in other embodiments, the drawn silica or glass fiber core delivers optical signals from the electrostimulation device to a convertor at a distal end of the lead which is configured and arranged to convert the optical signals into electrical signals to pace the heart. In still other embodiments, the plurality of sensing elements are optical or electrically based sensors to measure blood pressure, temperature, strain, fluid velocity, or intrinsic electrical activity. Moreover, in certain embodiments, at least one of the plurality of sensing elements is an optically-based pressure sensor that measures pressure through a sensing interferometer, dielectric mirror and mirrored pressure-sensitive diaphragm. The pressure sensor can include a piezoelectric element to measure blood pressure. Additionally, the metal cladding can be patterned to provide multiple discrete electrical conductors within the same metal layer, and the drawn silica or glass fiber core can be hollow. Further, in other embodiments, the multiple discrete conductors within the metal layer are in a spiral pattern around the circumference of the lead. In other embodiments still, the plurality of sensing elements are connected to the discrete metal conductors with radially placed conductive strands.

The various implementations and embodiments discussed above are consistent with the description of the figures below.

FIG. 1 shows schematically a human heart with some walls cut away. In FIG. 1 pacing leads are shown following a conventional path into the heart, and into the cardiac veins of the left ventricle, as has been typical of conventional practice and which, with some exceptions, is the basic path of leads of this disclosure.

In typical conventional practice, conductive leads 20, 21 and 22 are introduced into the heart through the superior vena cava 24, brought into the vena cava via subclavian or cephalic vein access points. For the right side of the heart, separate conventional pacing electrodes, as well as separate electrodes for biventricular pacing, are normally routed into the right ventricle, as well as the right atrium. For the left ventricle, typically a wire lead 21 would be brought from the right atrium 26 into the coronary sinus, and from there the leads are extended out into one or more coronary veins adjacent to the surface of the left side of the heart. The leads are not introduced directly into the interior of the left ventricle, which is the high-pressure chamber.

Pursuant to the disclosure, the routing of silica/glass fiber leads can be essentially the same as with conventional leads. An important difference is that the silica/glass fine wire lead, being much smaller in diameter than conventional leads, can be positioned deeper and more distally (also "retrograde" to normal blood flow toward the coronary sinus) within the target coronary vein. The coronary sinus/coronary vein architecture can be a relatively tortuous path, such that the physician will have an easier time manipulating a smaller diameter, flexible lead into the desired position within the coronary vein than for a larger diameter lead. Also, as a lead is manipulated deeper (more distally) within the coronary vein, the diameter of the vein becomes progressively narrowed. Thus, a smaller diameter lead can be placed deeper than a larger diameter lead. One theoretical reason why it is useful to place the terminal electrode of the lead in the deeper/distal/narrower portion of the coronary vein is because that portion of the vein apparently lies closer to myocardium. Thus, the cardiac muscle can perhaps be stimulated with less energy use when the electrode is closer to intimate contact with muscle overlying the coronary vein.

Figure 2:
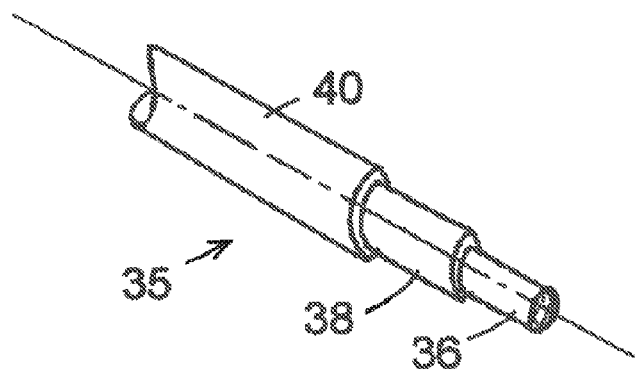
FIG. 2 is a schematic drawing in perspective showing an example embodiment of an implantable fine wire lead for a cardiac pulse generator such as a pacemaker, consistent with various aspects of the present disclosure.

FIG. 2 is a simple schematic showing an example of an implantable fine wire lead 35 pursuant to the disclosure, for subdermal connections from a pulsing device to the heart. In this form the lead 35 is unipolar. It has a drawn fiber core 36 of glass, silica, sapphire or crystalline quartz ("glass/silica" or "silica/glass") with a conductive metal buffer 38 over the fiber core. As discussed above, the buffer 38 is coated onto the fiber immediately upon drawing of the fiber, to preserve the strength of the fiber, protecting it from environmental elements such as atmospheric moisture that can attack the glass/silica surface and introduce fine cracking. Aluminum is a metal buffer 38 because of its hermetic bonding with the silica or glass surface, although gold or other suitable metals or metal alloys can be used. The aluminum buffer can be about 20 microns thick, 5 microns thick or even thinner. The wire lead 35 will have an electrode (not shown) at its distal end.

FIG. 2 also shows a polymer coating 40 as an outer buffer. This buffer is also added very soon after drawing, and is applied after the metal buffer 38 in a continuous manner. The plastic outer buffer coating 40 is biocompatible. As discussed further below, a further metal buffer can be added over the aluminum buffer 38 prior to addition of the plastic coating. This can be a coating of gold or platinum, for example, both of which are biocompatible. The plastic buffer 40 adds a further protective layer.

Figure 3:
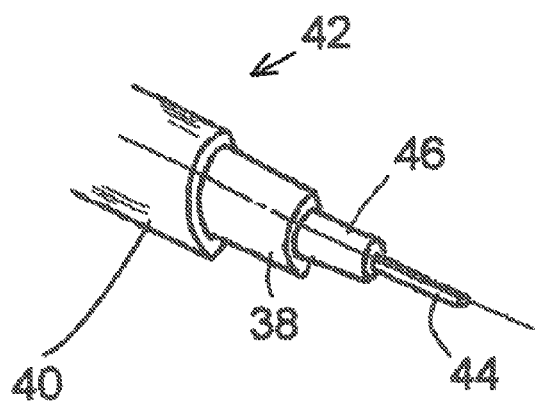
FIG. 3 is a similar view showing an example of a fine wire lead, consistent with various aspects of the present disclosure.

FIG. 3 shows a modified fine wire pacing lead 42 that has a metal conductor 44 as a center element. Here, the pure silica/glass fiber core 46 is drawn over the metal conductor 44. The process is well known, with a hollow glass/silica fiber first produced, then a metal conductive wire placed through the hole in the fiber and the glass/silica fiber drawn down against the wire. A conductive metal buffer is shown at 38 over the fiber, having been applied immediately on drawing of the conductor-containing fiber 46. An outer buffer coating of polymer material is shown at 40, being biocompatible and serving the purposes described above.

Figure 4:
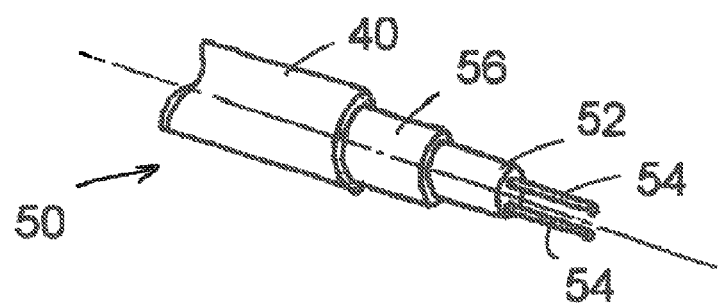
FIG. 4 is a view showing an example of a fine wire lead, consistent with various aspects of the present disclosure.

FIG. 4 is a similar view, but in this case showing a fine wire lead 50 formed of a glass/silica fiber core 52 formed over two metal conductors 54. The wire is pre-coated with a thin layer of glass before being co-drawn with the fiber. An aluminum buffer coating 56 surrounds the silica fiber 52, protecting the fiber from deterioration as noted above, and this can serve as a third conductive lead if desired. Again, an outer polymer buffer 40 provides an outer protective jacket and is biocompatible.

Figure 5:
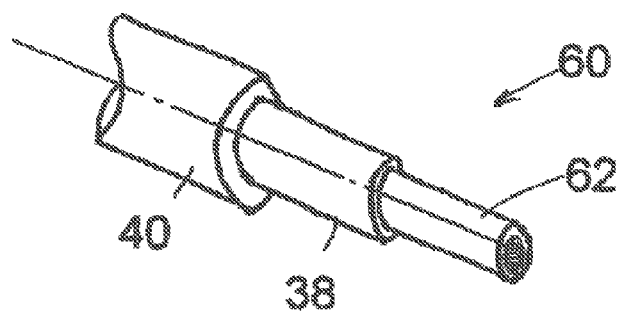
FIG. 5 is a view showing another example of a fine wire lead, consistent with various aspects of the present disclosure.

In FIG. 5 another example is shown of a fine wire pacing lead 60 of the disclosure. In this case the glass/silica fiber core 62 is hollow, allowing for better flexibility of the lead, and the lead construction is otherwise similar to that of FIG. 2.

Figure 6:
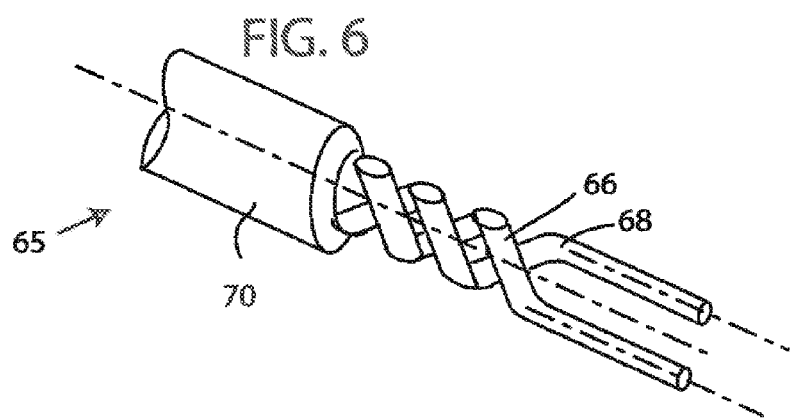
FIG. 6 is a view showing an example with twisted or braided multiple conductors, consistent with various aspects of the present disclosure.

FIG. 6 shows another example of a fine wire pacing lead 65 which has multiple glass/silica fibers 66 and 68 in a helical interengagement, twisted together. Each fiber 66, 68 comprises a glass/silica fiber conductor that can be similar to what is shown in FIG. 2, with or without a polymer buffer coating 40, or each could be constructed in a manner similar to FIG. 3, with or without a plastic buffer coating. Although two such fiber leads are shown, three or more could be included. The glass/silica fiber cores provide for strength and small-radius bending of the helical fiber 66, 68, and this type of braiding or helical twisted arrangement is known in the field of pacing leads, for absorbing stretching, compression or bending in a flexible manner. An outer polymer coating 70 protects the assembled fiber leads and provides biocompatability. The leads 66, 68 themselves can have the aluminum or other metal cladding as their outer layer, and/or they can have a further cladding of biocompatible metal or polymer.

Figure 7:
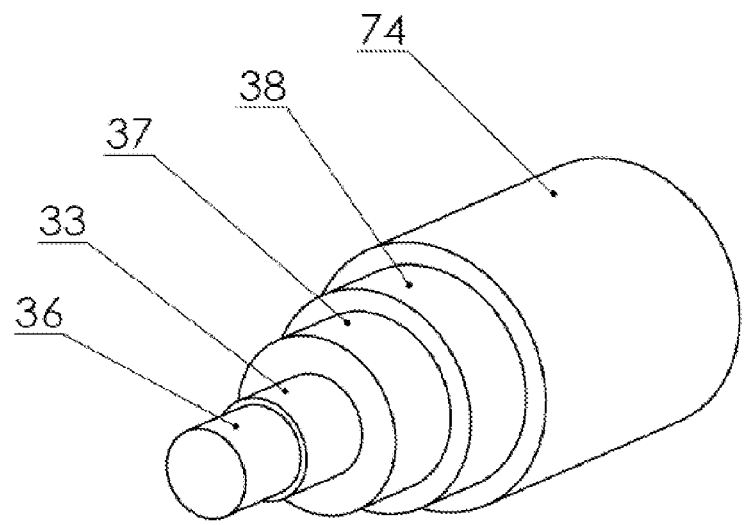
FIG. 7 is a schematic perspective view showing another example of a fine wire pacing lead, consistent with various aspects of the present disclosure.

FIG. 7 shows a section of a fine wire lead which is similar to that of FIG. 2, with a silica core 36, a carbon hermetic seal layer 33, a polymer layer (polyamide) 37, and a metal conductive cladding 38, but with a further biocompatible metal cladding 74 over the metal cladding. As noted above, this can be aluminum, gold or platinum, for example. The outer layer of polymer material is shown at 37.

Figure 8A:
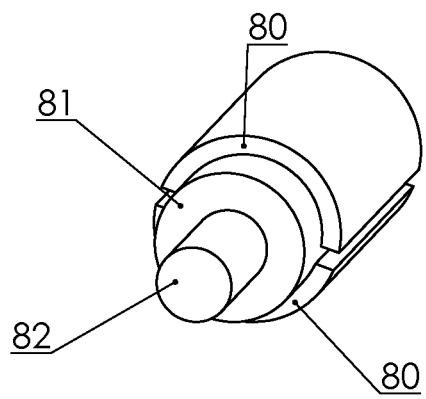
FIGS. 8A-8C are views showing examples of patterned metal cladding producing multiple conductive pathways, consistent with various aspects of the present disclosure.
Figure 8B:
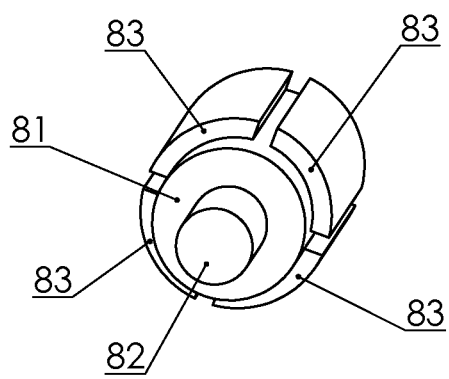
Figure 8C:
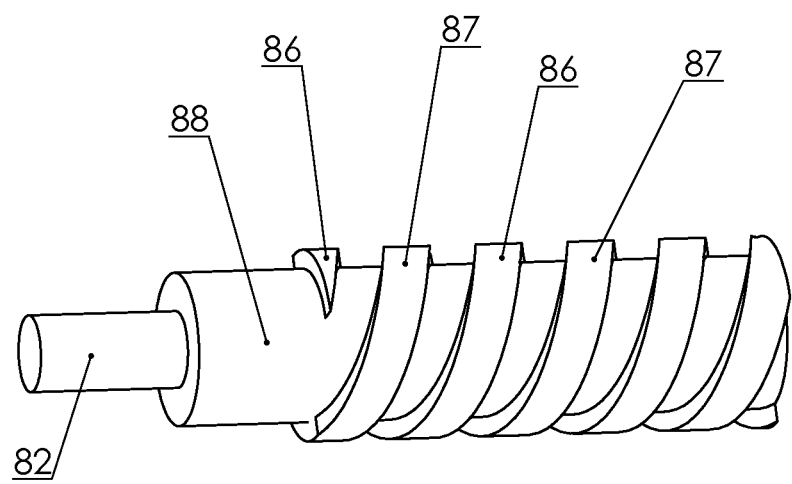

FIGS. 8A-8C depict a wire having multiple discrete conductive paths, consistent with the embodiments of the present disclosure. These figures represent a series of cross sectional views of several possible patterned metal depositions on fine wire leads. These pattern depositions are carried out using masks to apply the metal cladding or direct metal removal to produce two or more independent discrete electrically conductive paths down the length of the fine wire lead. Depicted are patterns involving two (FIG. 8A) or four electrically conductive paths 83 (FIG. 8B), made up of a single metal deposition, but may also represent deposition of two separate metals.

The metal cladding is formed to allow the conductive portions of the wire to be segmented into individually addressable conductors. Thus, different signals can be transmitted simultaneously (at approximately the same time) over the same fine wire lead but on different discrete conductors. The pattern for the metal cladding can be created using several manufacturing steps, a few non-limiting examples are described below.

In the first example, masking material can be applied to the fiber core 80 before the conductive metal cladding material is applied. The masking can be applied directly to the fiber core 82 or an underlying buffer 81 (carbon or other polymer material). The conductive metal material is then applied. The material of the mask are resistant to metal deposition and therefore the metal does not form on the material during the deposition process. In another instance, the metal cladding material is applied directly in the desired pattern to the fiber core through a screen-printing or similar process. In another instance, the strips are physically removed to create the breaks or desired pattern. This could be accomplished by laser removal or chemical process.

FIG. 8C shows the metal cladding to produce the multiple discrete conductive pathways 86 and 87 are applied in a spiral pattern on the fiber core or polymer/carbon buffer layer(s) 88. Each conductive pathway is independent and electrically isolated from all surrounding pathways. The spiral pattern is to provide shielding to reduce electromagnetic interference. Although this figure shows the conductive layer pattern applied to the inner buffer layer(s), such a conductive pattern could be applied to a second insulating layer applied over an inner conductive layer.

Figure 9:
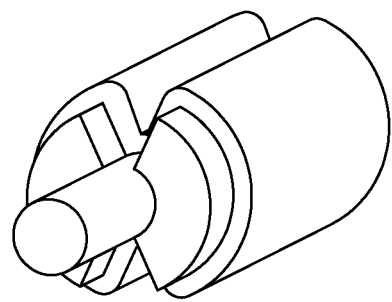
FIG. 9 is a sectional view showing a pattern of metal cladding with multiple conductive pathways, consistent with various aspects of the present disclosure.

FIG. 9 shows another example, in which the metal deposition process occurs with only a portion of the fiber core exposed to the source of the metal deposition. The portion can include different sides of the fiber core, each separated by a physical gap. Thereafter, the insulating material can be deposited over and between the deposited metal conductive portions.

Figure 10A:
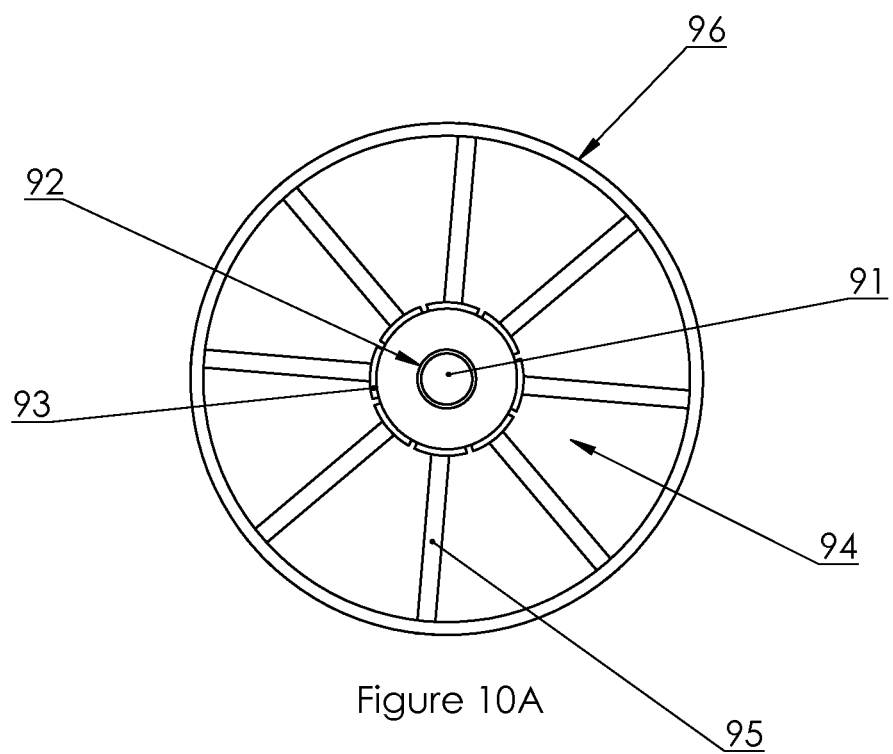
FIGS. 10A and 10B are sectional views of connections between multiple conductive pathways and electrodes/sensors, consistent with various aspects of the present disclosure.

FIG. 10A shows an end-on view of a central multi-conductor element. It includes a glass-core 91, an intermediate layer of carbon/polymide 92, a cladding of Ag metal 93, and a biocompatible polymer insulation layer 94. The Ag has been scribed to form 8 separate conductors. Each conductor 95 nominally occupies 45° of radial space. The size of this group of conductors is 0.005" to perhaps 0.020". Also shown is one of 8 longitudinal placed electrode rings 96 of approximately 0.053" (4-french). The 4-french is a common size for stimulation leads. Only the first of the 8 is depicted to electrically connect between the Ag conductors and the larger electrode ring is a flexible material doughnut or o-ring.

Figure 10B:
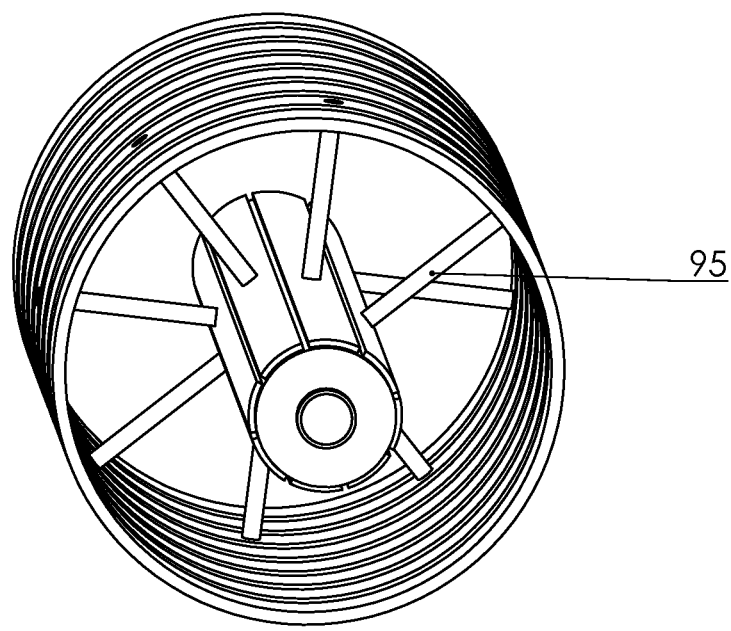

FIG. 10B depicts several radially placed conductive strands 95, preferably of a noble metal, but other metals are envisioned.

Figure 11:
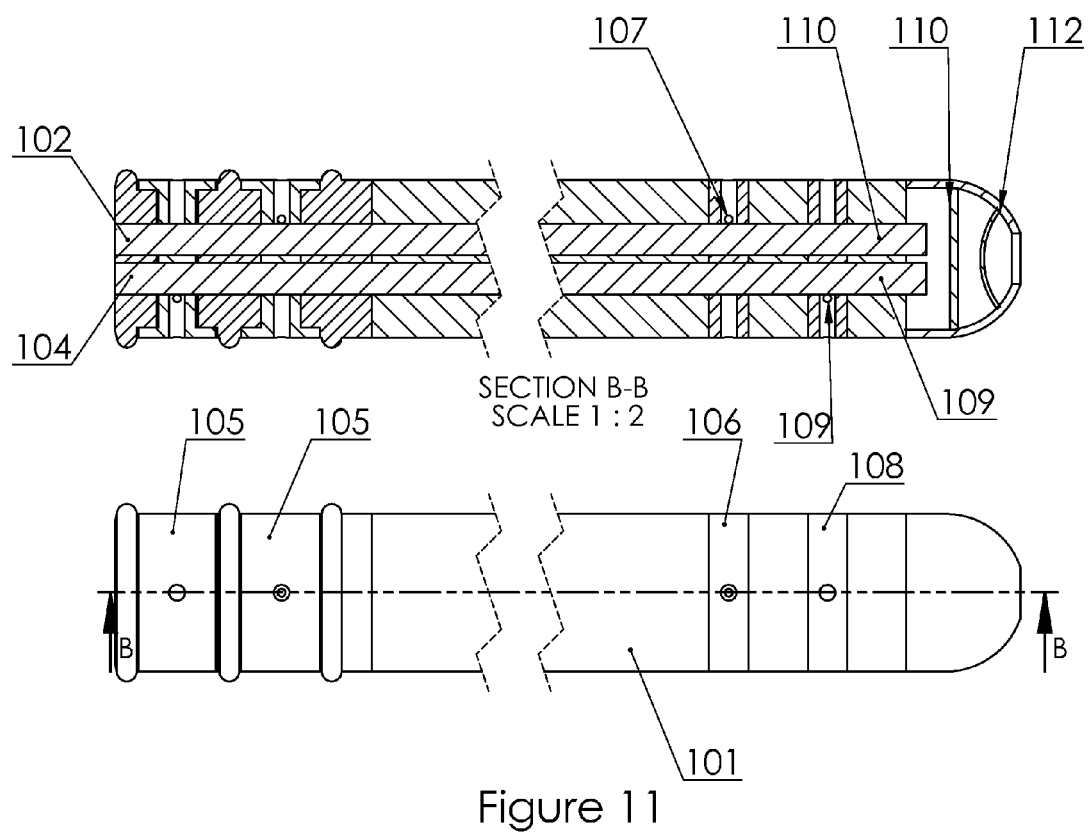
FIG. 11 is a view of a fine wire lead with an optical-based sensing element at a lead wire distal tip, consistent with various aspects of the present disclosure.

In FIG. 11, a bipolar electrically conductive glass or silica fine wire lead 101 is depicted, in which an optical-based sensing element is incorporated. The lead incorporates two distal electrodes, termed ring electrode 106 and tip electrode 108. These two electrodes make separate insulated electrical connections with lead bodies 104 and 102, respectively, which in turn make separate insulated electrical connections with electrodes in the standardized IS-1 or IS-4 connector 105 at the proximal end of the lead. One example of electrically conductive attachment of lead bodies 102 and 104 to tip 108 and ring 106 electrodes respectively is by way of welds 107 and 109. For purposes of illustration, a blood pressure sensor element is depicted at the tip of the lead, although sensing elements for other physiologically relevant parameters may be substituted or added. The sensor element in FIG. 10 incorporates a dielectric mirror 110 and a pressure sensitive mirrorized diaphragm 112.

Figure 12:
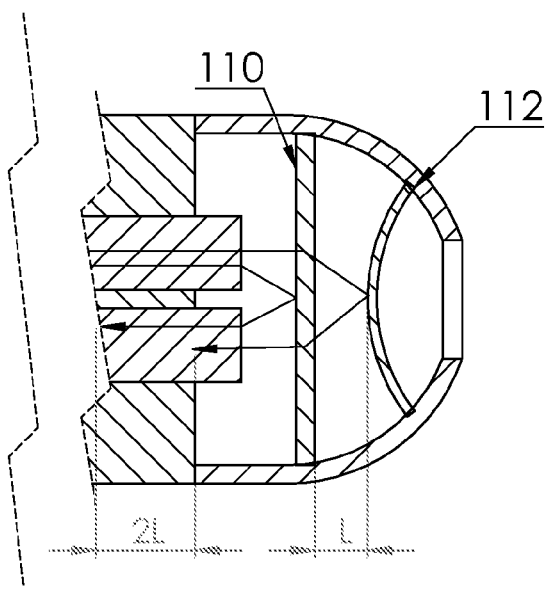
FIG. 12 depicts a close-up view of an optical-based sensing element as incorporated in a fine wire pacing lead, consistent with various aspects of the present disclosure.

FIG. 12 depicts details of an optical-based blood pressure sensor element which includes a dielectric mirror 110, a mirrored pressure-sensitive diaphragm 112. Also incorporated is a sensing interferometer that operates on the basis that incident light is both reflected by, as well as transmitted through, the dielectric mirror 110. Incident light energy reflected from the mirrored diaphragm 112 is such that it is offset from transmitted light reflected from the dielectric mirror 110, providing the dynamic interferometer path length necessary for correlation with changes in blood pressure.

Figure 13:
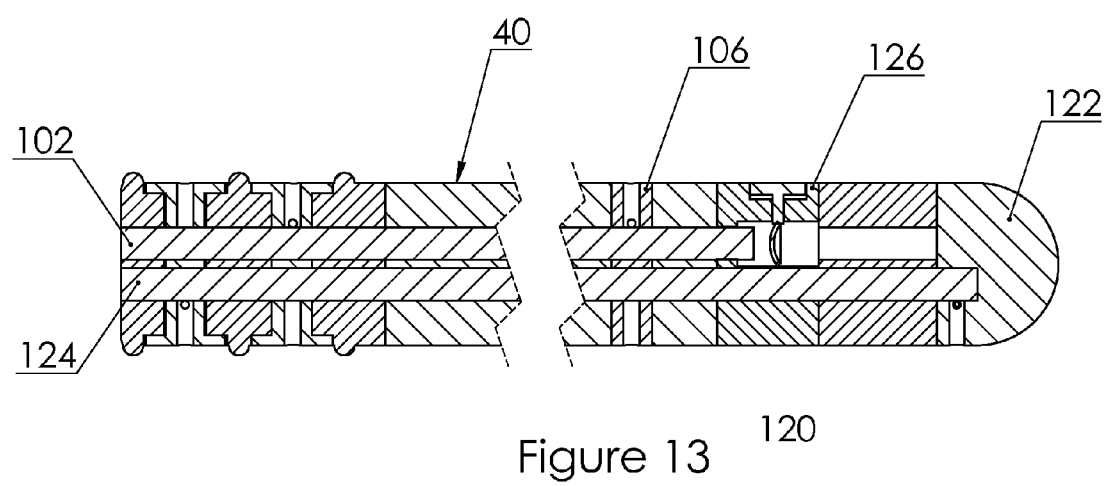
FIG. 13 is an alternate view of a fine wire lead incorporating a side-view optical-based sensing element adjacent to a lead wire distal tip, consistent with various aspects of the present disclosure.

Another example for a bipolar electrically conductive glass or silica fine wire lead 120 is depicted in FIG. 13, in which an optical-based sensing element 126 is incorporated in a side-view profile. The lead incorporates two distal electrodes, termed ring electrode 106 and tip electrode 122. In this example, the side-view sensing element 126 is located intermediate between the ring electrode 106 and the tip electrode 122. These two electrodes make separate insulated electrical connections with lead bodies 124 and 102, respectively, which in turn make separate insulated electrical connections with electrodes in the standardized IS-1 or IS-4 connector 105 at the proximal end of the lead. For purposes of illustration, a blood pressure sensor element 126 is depicted in side-view profile near the tip of the lead, although sensing elements for other physiologically relevant parameters may be substituted or added.

Figure 14:
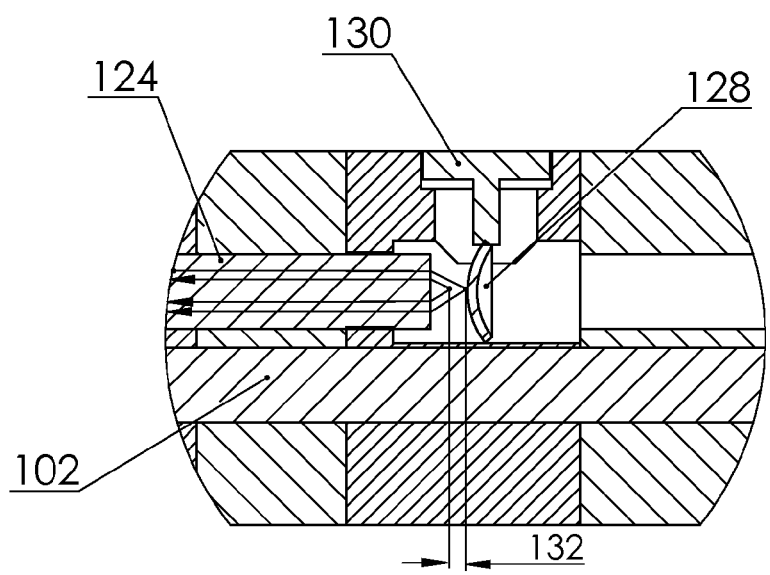
FIG. 14 depicts a close-up view of one example of a side-view optical-based sensing element, consistent with various aspects of the present disclosure.

FIG. 14 depicts details of an optical-based side-view blood pressure sensor element as shown in FIG. 12. This example incorporates a central mirrored pressure-sensitive diaphragm 128. The central diaphragm 128 is physically connected with sensor element 130, which makes contact with blood. Sensor element 130 undergoes physical shape change in response to changes in blood pressure. The physical shape changes induced in sensor element 130 are then transferred to diaphragm 128. The extent of shape change in diaphragm 128 correlates with blood pressure. The mirrored surface of the sensor element 130, which faces towards lead body 124, moves in relation to the lead body in response to dynamic changes in blood pressure. This movement 132 provides the basis for optical-based sensing of blood pressure.

Figure 15:
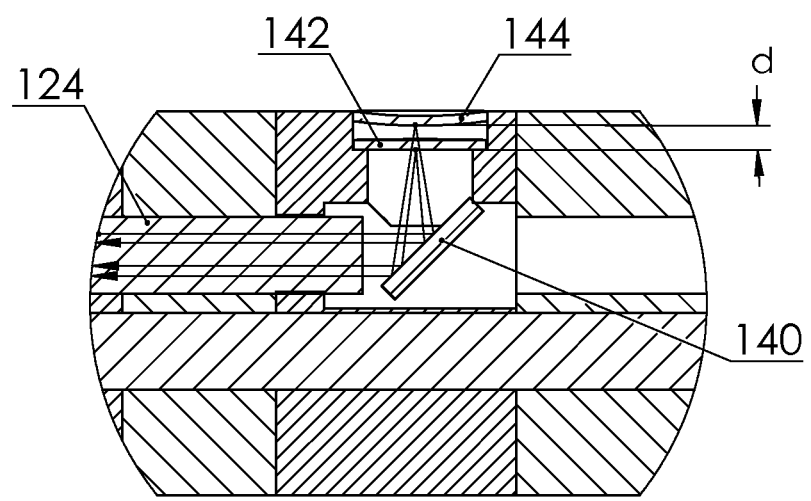
FIG. 15 shows a close-up view of another example for a side-view optical-based sensing element, consistent with various aspects of the present disclosure.

FIG. 15 depicts details of another example for an optical-based side-view blood pressure sensor element. This example incorporates a dielectric mirror 142 and a mirrored diaphragm 144, similar in function to the dielectric mirror 110 and mirrored diaphragm 112 in FIGS. 9 and 10. The difference is in orientation. Whereas dielectric mirror 110 and mirrored diaphragm 112 are oriented generally perpendicular to the central axis of the fine wire lead, the dielectric mirror 142 and mirrored diaphragm 144 are oriented generally parallel with the central axis of the fine wire lead in the present example.

The dielectric mirror 142 and mirrored diaphragm 144 operate on the same basis as described in FIG. 10 in providing a dynamic interferometer for correlation of diaphragm shape change with changes in blood pressure. A central mirror 140, oriented roughly 45 degrees to the central axis of the lead enables incident light energy to contact the dielectric mirror 142 and mirrored diaphragm 144, as well as reflected light energy to pass unimpeded along the lead body 124.

Figure 16:
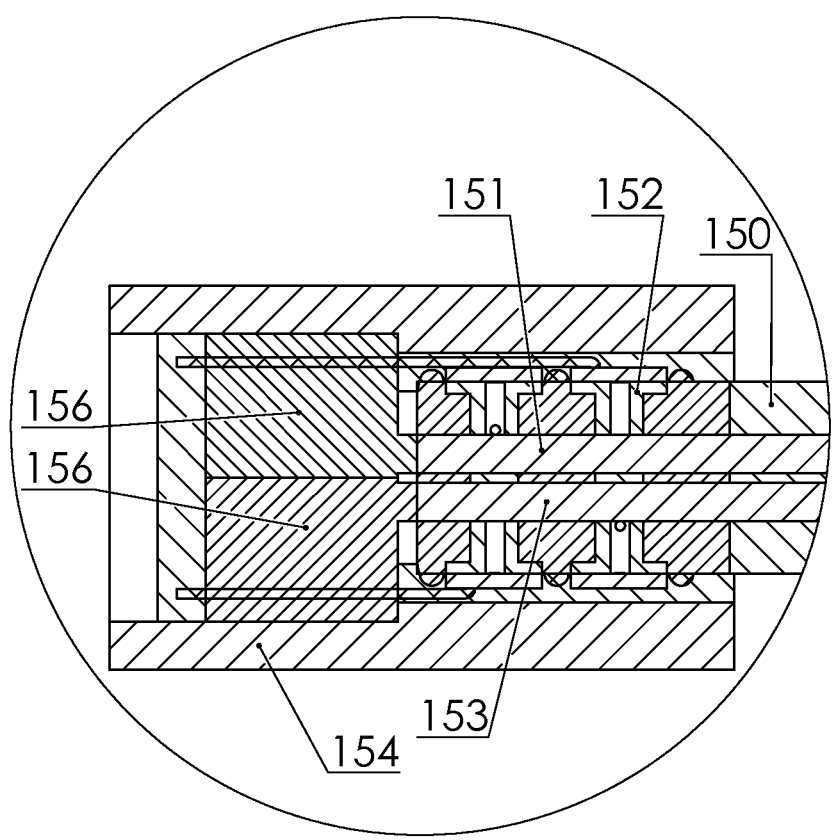
FIG. 16 shows a close-up view of a connection for a bipolar fine wire lead capable of optical-based sensing, with a standardized connector adapted for optics, consistent with various aspects of the present disclosure.

FIG. 16 shows a close-up view of a connection for a bipolar fine wire lead capable of optical-based sensing 150, with a standardized connector adapted for optics 152. Specific contacts are made between electrically conducting lead bodies 151 and 153 and electrical connections within the IS-1 or IS-4 connector, as well as an optical connection between an optically-enabled electrically conductive lead body and a sensor drive/sensor processor 156.

Figure 17A:
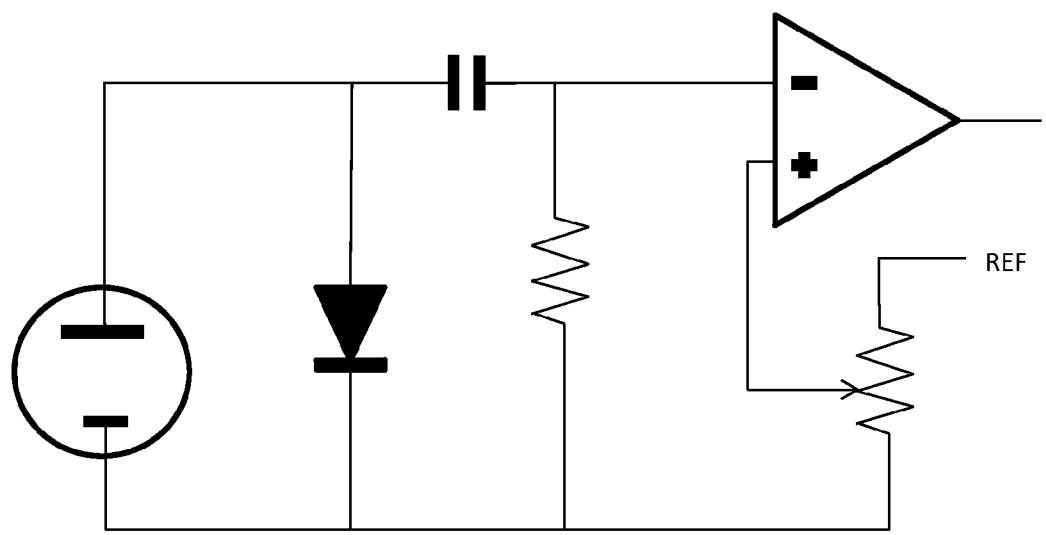
FIGS. 17A and 17B show a schematic and a view of an optical-based pacing example using a fine wire lead, consistent with various aspects of the present disclosure.

FIG. 17A depicts an example of the electrical circuit where the light energy transmitted through the optical fiber is collected by the photovoltaic cell which then converts it into an electrical stimulation pulse.

Figure 17B:
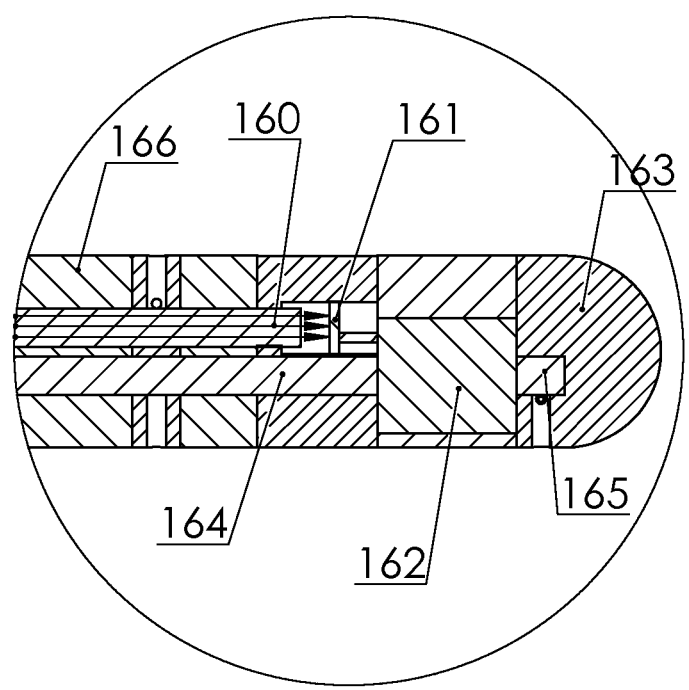

FIG. 17B depicts an example of an optical-based pacing lead 166 consisting of an optical fiber 160, photovoltaic cell 161, lead control circuitry 162, and pacing electrode 163. The light pulse is transmitted from the light generator through the optical fiber 160. The optical fiber can include a metal cladding, a buffer made of carbon, polymer or other suitable material. The optical fiber can also include an additional glass cladding (not shown) using a glass or silica of lower index of refraction to increase total internal reflection and maximize light transmission. At the distal end of the optical fiber, a photovoltaic cell 161 is positioned to absorb the transmitted light. The photovoltaic cell transforms the light energy into electrical energy. The electrical energy is transferred through the lead control circuitry 162 where it is stored in a capacitor or other electrical circuit design. At the desired time, the electrical energy (pacing pulse) is discharged through the lead control circuitry to the pacing electrode 163 through conductor 165. The timing, amplitude, and duration of the pacing discharge can be controlled by the intensity or another characteristic of the transmitted light signal, or by a timing element within the electrical control circuitry. The pacing pulse can also be controlled by the implanted generator through connection to the lead control circuitry 162 by way of an electrical conductive pathway built within the fine wire lead, such as the metal cladding 164.

The entire assembly can be coated with a polymer, silicone, or other biocompatible material to insulate and protect it from the body.

For further discussion of the flexible and durable fine wire lead, as relating to the embodiments and specific applications discussed herein, reference may be made to the provisional patent applications (61/614,169 and 61/742,280) to which priority is claimed. The aspects discussed therein may be implemented in connection with one or more of embodiments and implementations of the present disclosure (as well as with those shown in the figures).

Based upon the above discussion and illustrations, those skilled in the art will readily recognize that various modifications and changes may be made without strictly following the exemplary embodiments and applications illustrated and described herein. Furthermore, various features of the different embodiments may be implemented in various combinations. Such modifications do not depart from the true spirit and scope of the present disclosure, including those set forth in the following claims.

What is claimed is:

1. An apparatus comprising:
   an implantable electrostimulation device; the implantable electrostimulation device selected from the group consisting of a cardiac pacemaker, cardioverter-defibrillator, and a cardiac resynchronization therapy device;
   a plurality of sensing and pacing elements; and
   a fiber optic lead extending in a sealed relationship from the electrostimulation device to the plurality of sensing and pacing elements, the fiber optic lead having multiple discrete conductors and a drawn fiber core comprising silica or glass, a polymer cladding on the fiber core, and a coaxial conductive metal layer over the polymer cladding, wherein the fiber optic lead is configured and arranged to simultaneously deliver an electrical signal to or from a first sensing and pacing element and an optical signal to or from a second sensing and pacing element.

2. The apparatus of claim 1, wherein
   an outer diameter of the fiber optic lead at the metal layer is no greater than about 750 microns, and the fine wire lead is sufficiently flexible to bend to a radius of about 8 to 10 times the fiber core's diameter without damage.

3. The apparatus of claim 1, wherein the coaxial conductive metal layer comprises a conductive metal configured and arranged to deliver electrical signals between the electrostimulation device and at least a first sensing and pacing element, and further including a biocompatible insulating coating covering the fine wire lead.

4. The apparatus of claim 1, wherein
the conductive metal is comprised of silver, and the polymer cladding is comprised of carbon.

5. The apparatus of claim 1, further comprising a control hub, the control hub configured and arranged to interconnect to the fine wire conductor.

6. The apparatus of claim 1, wherein
at least one of the plurality of sensing elements is an optically-based pressure sensor configured and arranged to measure pressure through a sensing interferometer, dielectric mirror or mirrored pressure-sensitive diaphragm.

7. The apparatus of claim 6, wherein the pressure sensor is configured with a piezoelectric element to measure blood pressure.

8. The apparatus of claim 1, wherein the metal cladding is patterned to provide multiple discrete electrical conductors within the same metal layer.

9. The apparatus of claim 8,
wherein the plurality of sensing elements are connected to the discrete metal conductors with radially placed conductive strands.

10. An apparatus comprising:
an electrostimulation device;
a plurality of sensing and pacing elements;
a fiber optic lead including
a drawn fiber core comprising silica or glass,
a cladding, on the fiber core, the cladding comprising a carbon hermetic seal material,
a coaxial conductive metal layer, on the cladding, configured and arranged into multiple discrete conductors, and
a biocompatible coating configured and arranged to seal the fine wire lead,
wherein the fine wire lead extends in a sealed relationship from the electro stimulation device to the plurality of sensing and pacing elements, and the fine wire lead is configured and arranged to simultaneously deliver electrical signals and optical signals between the sensing and pacing elements and the electrostimulation device.

11. The apparatus of claim 10, wherein
an outer diameter of the fiber optic lead at the metal layer is no greater than about 750 microns, the fiber core has a diameter no greater than about 450 microns,
the fine wire lead is sufficiently flexible to bend to a radius of about 8 to 10 times the fiber core diameter without damage.

12. The apparatus of claim 10, wherein
the conductive metal layer is a conductive metal configured and arranged to deliver electrical energy or signals between the electrostimulation device and a sensor or pacing element,
the conductive metal is silver, and
the electrostimulation device is one of a cardiac pacemaker, cardioverter-defibrillator, cardiac resynchronization therapy device or cardiac diagnostic device.

13. The apparatus of claim 10, wherein
the fiber core is configured and arranged to deliver optical signals from the electrostimulation device to a convertor at a distal end of the lead which is configured and arranged to convert the optical signals into electrical signals to pace the heart.

14. The apparatus of claim 10, wherein at least one of the plurality of sensing and pacing elements is an optically-based pressure sensor configured and arranged to measure pressure through a sensing interferometer, dielectric mirror and mirrored pressure-sensitive diaphragm.

15. The apparatus of claim 14, wherein the optically-based pressure sensor is configured with a piezoelectric element to measure blood pressure.

16. The apparatus of claim 10, wherein the coaxial conductive metal layer is in a spiral pattern around the circumference of the lead, the spiral pattern being adapted to provide EMI shielding.

17. The apparatus of claim 16, wherein the sensing elements are connected to the discrete metal conductors with radially placed conductive strands.

18. The apparatus of claim 10, further including a biocompatible insulating coating covering the fine wire lead.

19. The apparatus of claim 10 wherein at least one of the plurality of sensing and pacing elements is an optical based sensor configured and arranged to measure at least one of blood pressure, temperature, strain, fluid velocity, and intrinsic electrical activity.

20. The apparatus of claim 10 further comprising a converter that converts an electric current into an optical signal, wherein the fiber core is configured and arranged to deliver the optical signal to the electrostimulation device.

* * * * *